United States Patent [19]
Erb

[11] Patent Number: 4,590,579
[45] Date of Patent: May 20, 1986

[54] APPARATUS AND METHOD FOR DIGITAL SPECIFIC GRAVITY MEASUREMENT

[75] Inventor: Tom L. Erb, Austin, Tex.

[73] Assignee: Ramsey Engineering Company, St. Paul, Minn.

[21] Appl. No.: 539,045

[22] Filed: Oct. 4, 1983

[51] Int. Cl.$^4$ .......................... G01N 7/00; G01N 9/00
[52] U.S. Cl. ..................... 364/558; 328/163; 364/554; 364/574; 375/103; 378/54
[58] Field of Search ............... 364/554, 558, 574; 73/32 R; 378/54, 55, 56; 328/163, 165, 167; 375/99, 102, 103

[56] References Cited

U.S. PATENT DOCUMENTS

| | | | |
|---|---|---|---|
| 3,832,550 | 8/1974 | Bartlett et al. | 378/56 |
| 3,832,551 | 8/1974 | Bartlett et al. | 378/54 |
| 3,947,636 | 3/1976 | Edgar | 328/163 X |
| 4,301,366 | 11/1981 | Bertin et al. | 378/54 X |

*Primary Examiner*—Errol A. Krass
*Assistant Examiner*—Kevin J. Teska
*Attorney, Agent, or Firm*—Norvell & Associates

[57] ABSTRACT

A device is provided for enabling the signal generated by a sensing device to be presented which is representative of the property sensed of a flowing material over a conveyor, or the like. The output is presented for observation and/or as a usable input to control means responsive to the sensed property. A pair of signals, one with a slow time constant, the other with a fast time constant, is derived from the sensing device signal. An output signal is in turn derived from one of the two signals, normally the slow. From the event rate in the sensing device, the expected statistical deviation is computed and utilized as the threshold of divergence of the pair of signals. When the divergence exceeds the threshold, the fast signal is switched to be the same value as the slow signal so that no perceptible perturbation appears in the output and the output signal is derived from the fast signal. At the next and each successive fast time constant, if the convergence still exists, the slow signal is set equal to the fast signal. When the divergence ceases, the value of the slow signal is switched to be the value of the fast signal and the output is switched to come from the slow signal for stable representation of a stable condition.

12 Claims, 5 Drawing Figures

APPARATUS AND METHOD FOR DIGITAL SPECIFIC GRAVITY MEASUREMENT

BACKGROUND OF THE INVENTION

1. Field of the Invention

The present invention relates to a dynamic process tracking device, and, in particular, to an apparatus for presenting an output with minimal effects of the compromise between providing precision and stability and being capable of responding to rapid changes without any apparent perturbations.

2. Description of the Prior Art

In many industries, it is desirous to measure the density or level of a process material through or over a conduit or conveyor. It is desirous to isolate the measuring means from the material being measured. One solution to the problem has been the use of a nuclear emitter of gamma rays to be mounted in proximity to the container of the material. A sensing device is located appropriately to receive the gamma rays that pass through the material to be examined.

Previously, the output of the sensing device was filtered to minimize the statistical nature of the radiation. This led to inaccuracies in the output as well as to improper operation of devices utilizing such output to operate control devices in response to the sensed signal during rapid changes in the material parameter being measured.

SUMMARY OF THE INVENTION

The present invention relates to a device for handling incoming signals from a radiation detector which senses when the change that is occurring in that signal is the result of the parameter being measured and not simply the result of the statistical deviations of the signal itself, due to the statistical nature of the radiation activity.

DESCRIPTION OF THE PREFERRED EMBODIMENTS

Figure 1:
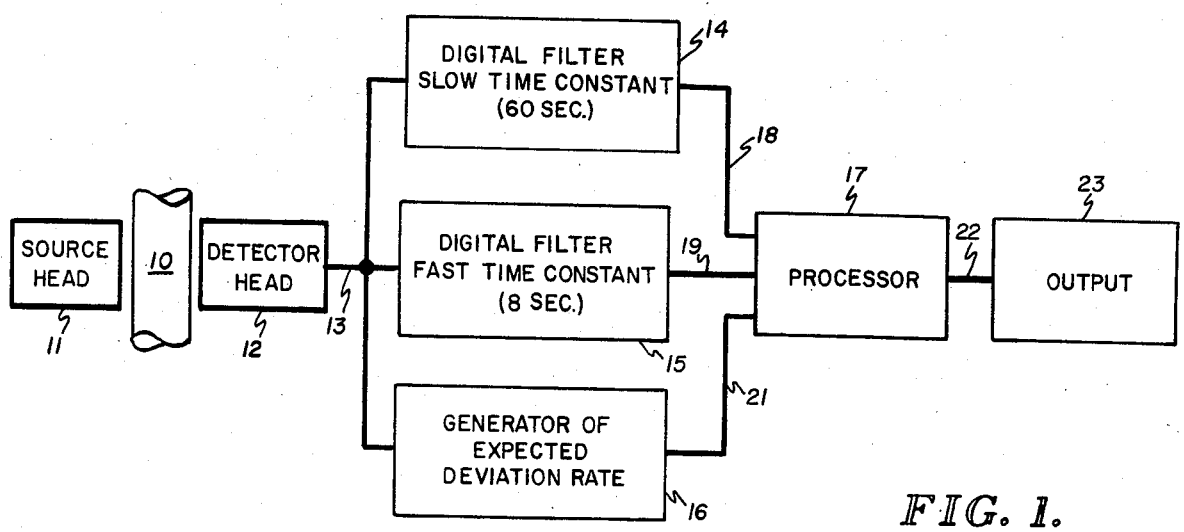
FIG. 1 is a block diagram of a dynamic process tracking indicator.

There is shown in FIG. 1 a dynamic process tracking indicator system, the apparatus for digital specific gravity measurement, according to the present invention. The system is utilized to provide a very stable signal representation of the measurement of material density, in this example, in a pipe 10. The moving mass could be carried by a conveyor belt or some other device, as required. A gamma ray source head 11 is secured with a gamma ray detector head 12 on opposite sides of a pipe 10. The detected signal generated by the gamma ray detector head 12 is conducted through connector 13 to a digital filter with a slow time constant 14, a digital filter with a fast time constant 15 and a generator for the expected deviation rate 16. The output of the digital filter 14 is connected as an input to the processor 17 through a connector 18. The output of digital filter 15 is connected as an input to the processor 17 through 19. The output of the generator 16 is connected through a connector 21 as a third input to the processor 17. The output of the processor 17 is connected through a connector 22 as the system output 23.

Figure 5:
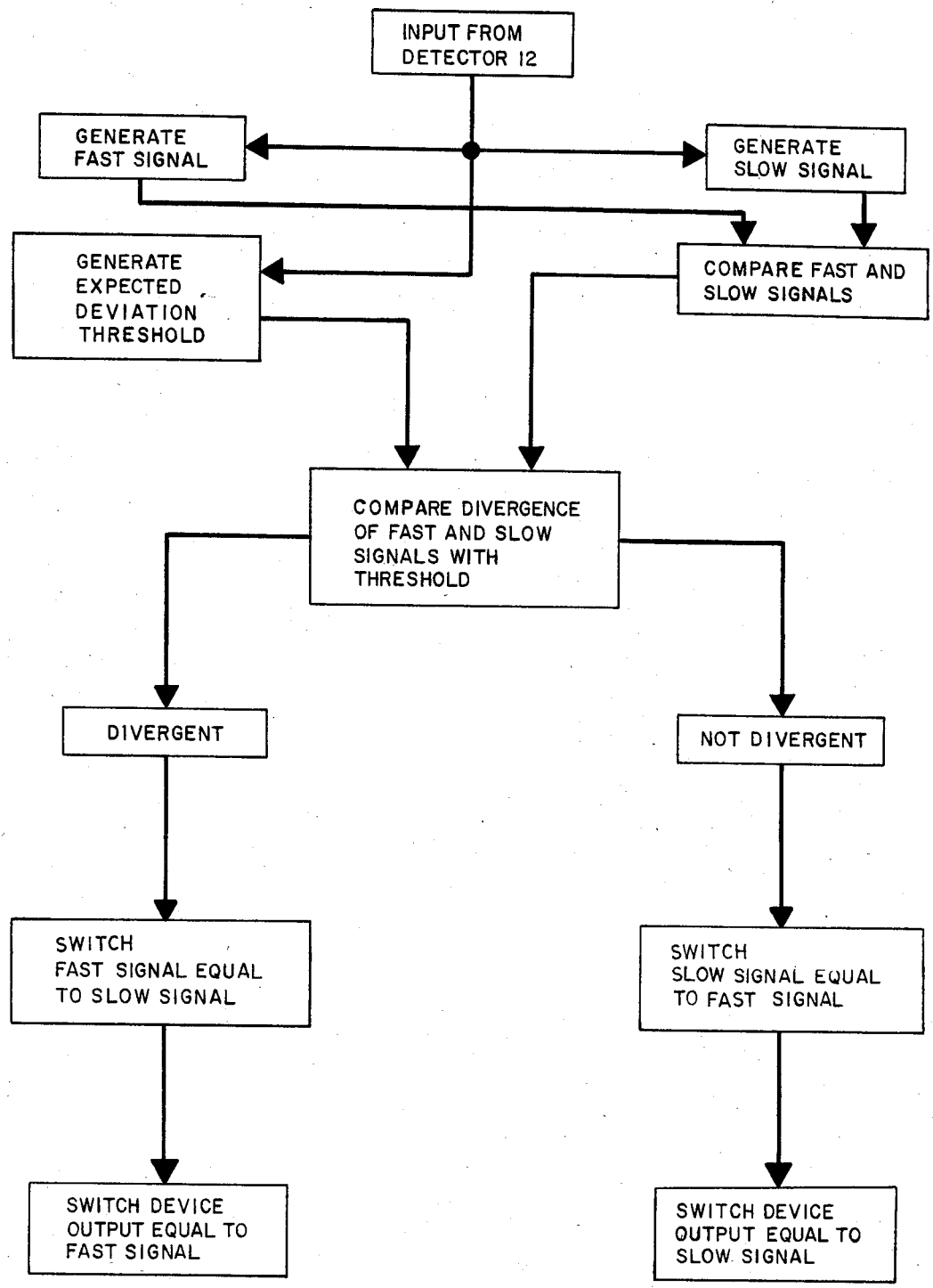
FIG. 5 is a flow diagram of the operation of the processor in FIG. 1.

FIG. 5 shows the flow diagram of the operation of the processor 17 shown in FIG. 1. This operation requires means for switching the value of the system output to be the same as the output of the digital filter with a slow time constant 14, means for switching the output system value to be the same as the outut of the digital filter with a fast time constant 15, means for comparing such slow and fast signals with each other, and means for comparing any divergence of such a slow and fast signal wth a divergence threshold as established by the expected deviation rate generator 16 in FIG. 1.

OPERATION

The general operation of the dynamic tracking indicator as applied to a density gauge function illustrated in FIG. 1 is illustrated in the simplified flow diagram of FIG. 5.

Before discussing the flow diagram of FIG. 5, it should be noted that the basic problem to be solved is the compromise in radiation based instrument configuration involving density, level, thickness, and the like, measurement. Fundamentally, radiation measurements, which involve measuring the amount of radiation received at a detector, require the accumulation of sufficient events of interaction between the radiation and the detector to establish sufficient statistical confidence in the measurement. In particular, the standard deviation of the measurement is equal to one over the square root of the number of counts or events accumulated. This means, for a given event rate which relates to the efficiency of the detector and the size of the source and how much absorbing material has to be penetrated, the statistical precision is a function of the accumulation time or, on a continuous measurement, the continuous averaging of the received radiation. It is the function of the exponential time constant that is typically used to average the signal. An exponential time constant is most commonly used for this type of instrument. This means that, given a step change in the parameter of interest, the measuring device responds to within one over e, that is, exponential e, within one time constant. It may take three to five time constants to get fairly close to the ultimate output. For faster response, a sacrifice of statistical precision may be necessary.

The essence of this invention is to minimize the effects of this compromise by configuring a system that will have the stability or precision associated with a long time constant during stable measurement conditions, but will sense when the measurement conditions are changing and provide an output that responds with a much faster time constant. This is accomplished without any apparent bumps or perturbations in the output signal.

This invention is readily incorporated into a commercially available series density gauge which provides density control, percent solids control, mass flow measurement, and control and other functions. Many other devices can utilize this dynamic tracking device. It also is possible to implement this device in analog equipment.

The technique involves simultaneously processing two input signals derived from the output of the radiation detector 12 with two different digital filtering constants to, in effect, carry two signals; one fast signal 19 and one slow signal 18. The slow signal 18, is well damped and, thus, is statistically smooth; and the fast signal 19 is more responsive to the changes in the input and is not statistically smooth. In a particular embodiment, the factor of eight to one in the ratio of the constants of the two signals is selected. Eight turns out to be a reasonable compromise between the responsiveness and the statistics. Statistical deviation relates to the square root of the time constant. For example, a signal which is sixteen times faster than another, or which has a one sixteenth time constant, will have a statistical deviation four times worse. With an eight to one deviation, almost three times, or the square root of eight, worse.

In the present invention, the difference between the fast and the slow signals is constantly monitored as shown in FIG. 5. On the average, the signals should be equal since they are based on the same incoming signal. On an instantaneous basis, the difference between the two signals will simply be due to the statistical deviations, in that one has a worse statistical deviation than the other. Although it is mathematically possible for the two to be arbitrarily different, it is probable that in a new unit of time, a greater difference than the threshold will be detected. This probability decreases rapidly with a plurality of standard deviations.

When the difference between the two signals is greater than some predetermined limit, or the threshold set by the expected deviation generator, typically four or five standard deviations of the fast signal, the output is switched over to and is based on the fast signal rather than the slow signal. This is because the difference is interpreted to mean that there is a change in the input that could not be reasonably determined to be the result of statistical deviations. The fast signal tracks more responsively than the slow signal. However, this procedure results in what, in the industry, is called "bumping the output." In other words, a step in the output will be set since the two signals are different from each other. If the slow suddenly is switched to the fast, there will be an increased step in the output that is unacceptable. The output must respond in a smooth and coherent fashion. This bumping is eliminated by determining that the process is in fact changing, and the change that is seen is due to the process rather than the statistics; that is, the change is based on the difference between the two signals. Then, instantaneously, the value of the fast signal is set to be equal to the value of the slow signal. Then the output of this device is switched over to the fast signal. Since at this moment the fast and slow signals are equal, the output does not get perturbation. During this valid process change, the output changes as the fast signal changes, even if it is momentarily equal to the slow signal.

For any particular configuration, there are: a fast time constant; and a slow time constant, i.e., two signals. At one fast time constant after a switch over has occurred, the difference between the fast and slow is again examined. If the difference is still greater than the appropriate number of deviations, the input is known to be still changing because the two are still diverging from each other. During this process change, the output signal continues to operate from the fast signal. However, the slow signal value is arbitrarily set to be equal to the fast signal, after each new divergence determination, so that at that time, they are equal and another fast time constant later, they are examined again to see if they are still diverging. This process is continued every fast time constant with the slow being set equal to the fast, and reexamined every time constant later to determine if the divergence is continuing. If the examination indicates that divergence has ended, that is, the difference between the two is within the appropriate number of deviations, the slow is then set equal to the fast to avoid a bump, and the output is switched back over to the slow so that the output will reveal the essentially stable process conditions. It is easy to see that this process takes advantage of the slow signal going along with small deviations and the fast signal going along with somewhat larger deviations.

Figure 2:
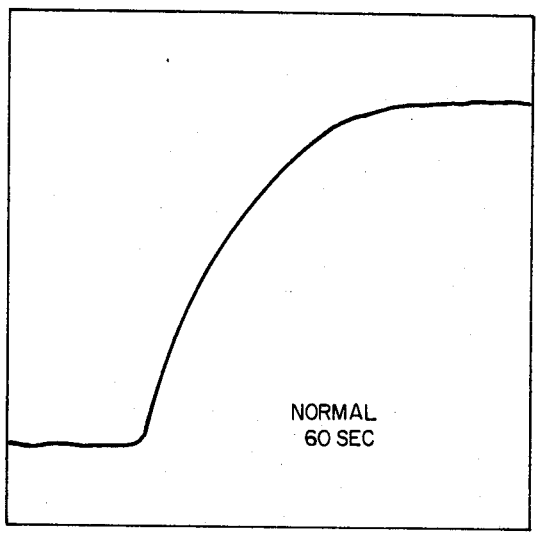
FIG. 2 is a representative output of the slow time constant digital filter.
Figure 3:
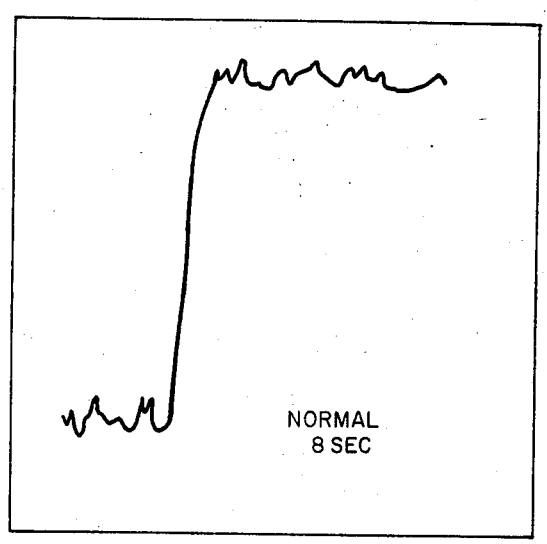
FIG. 3 is a representative output of the fast time constant digital filter.
Figure 4:
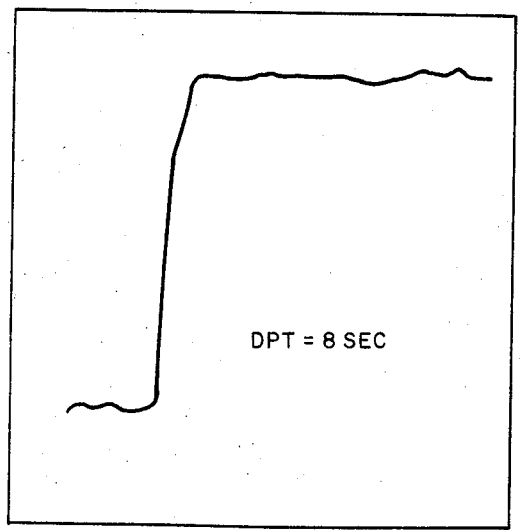
FIG. 4 is a representative output of the dynamic process tracking indicator.

Turning now to FIGS. 2, 3, and 4, there is a presentation of the outputs of the slow, the fast and the device output signals. The slow signal, FIG. 2, proceeds having relatively small deviations. In FIG. 3, the fast signal has the same average but has somewhat larger deviations. When a change in the input process occurs, the slow signal will begin to move slowly to approach such change while the fast signal will begin to move considerably more rapidly to approach the change. The difference in the signals is continually monitored. When the difference exceeds the threshold of the expected deviation, the fast signal is set to equal the slow signal. The device output, as seen in FIG. 4, is made up of the relatively noise-free slow signal in this beginning horizontal travel, and the sharp rise is made up of the responsive fast signal. There is no bump at the changeover point, because the fast signal was set to equal the slow signal. Thus, the sharp rise. The device output continues at a higher slope. At one fast time constant, the difference is again examined. If the difference is still significant, the slow is set to be equal to the fast and continue to operate off the fast. But now, this gives a point from which test divergence, and the process, is continued until this difference is no longer significant. All this time, the output has been operating from the fast signal.

When the difference is no longer significant, that is, the divergence ceases, the fast and slow signals are set to be equal so that a bump will not occur as the output signal again becomes horizontal, and the device output is switched over to the slow signal for the shown smoothness.

It is to be noted that the statistical deviation that is expected on a signal is computable since it is based on the event rate in the detector. As the signal level changes as the result of the changes in the detector, the statistical deviation on that signal will also change. In the system, the expected deviation level is continuously recomputed based on the signal strength processed in the expected deviation generator 16. The deviation between the two signals at which transitions are activated is continually changed as a function of the threshold computed in the expected deviation generator. Therefore, exmaining for deviation between the fast and the slow signals, and also continuous computing what that expected deviation should be, with the accompanying change of the threshold of the transition, are occurring simultaneously.

Turning to FIG. 5, the operation of the device is such that the output signal of a radiation detector is filtered so that two signals emanating therefrom, one with A slow time constant, the other with a fast time constant, are tested for convergence every fast time constant to see if the divergence exceeds the threshold established by the expected deviation threshold generator. The threshold represents the level of statistical noise, thereas higher divergent counts reveal that the input source is indeed sensing a change in the process.

If the fast and slow signals are indeed found to be divergent, the fast signal is set to be equal to the slow signal so that the transition will be smooth, and the device output will be switched to be equal to the fast signal. Examination will recur every fast time cycle and the device output will follow the fast signal until divergence is no longer detected. Then the fast signal will be switched to be equal to the slow signal, and device output will be switched to be equal to the slow signal.

Although the invention has been described in terms referring to a specific gravity measurement, it should be understood that this is by illustration only and that the invention is not necessarily limited thereto, since alternate embodiments and operating techniques will be come apparent to those skilled in the art in view of the disclosure. Accordingly, modifications are contemplated withich can be made without departing from the spirit of the described invention.

What is claimed and desired to be secured by Letters Patent is:

1. A dynamic tracking device for controlling a process by minimizing statistical deviation in the output of a radiation detector for controlling a process, said tracking device comprising: means for filtering to generate a fast time constant signal from the output of said detector; means for filtering to generate a slow time constant signal from the output of said detector; means for determining divergence of said fast and slow signals; and processor means responsive to said divergence to switch between the values of the two said signals to produce a smooth and coherent device output.

2. The dynamic tracking device of claim 1 further comprising: means for determining the threshold of statistical deviation present in said output of said detector wherein processor means compares the threshold and the divergence of said fast and slow signals, whereby said means responsive to said divergence is operative in response to a divergence on a real time basis.

3. The dynamic tracking device of claim 1 further comprising: said processor means is operative to switch the value of the fast signal to be the value of the slow signal when perturbations are to be avoided.

4. The dynamic tracking device of claim 1 further comprising: said processor means is operative to switch the value of the device output to be equal to the value of the fast signal during process changes; and said processor means is operative to switch the value of the device output to be equal to the value of the slow signal during periods of absence of process changes.

5. The dynamic tracking device of claim 1 wherein said smooth and coherent device output is provided by: said processor means is operative to switch the value of the fast signal to be the value of the slow signal during the fast time constant following a divergence of said fast and slow signals; and said processor means is operative to switch the device output to be equal to the fast signal if the divergence is continued; said processor means is operative to switch the value of the fast signal to be the value of the slow signal following the end of a divergence of said fast and slow signals; and said processor means is operative to switch the device output to be equal to the slow signal following the end of said divergence.

6. A dynamic tracking device for determining the density of a material flowing past a station comprising: a nuclear radiation source means; a radiation detection means aligned to receive radiation from said source means; a material flow passing between said source means and said detection means; first filter means connected to said detection means for providing the output of said detection means with a slow time constant signal; means for generating from the fast and slow constant signals based on said output signal an expected deviation threshold; means for determining the difference between said fast and slow signals every fast time constant; means for comparing said difference with said threshold to determine material flow changes; said processor means responsive to a material flow change is operative to switch the value of the fast signal to be equal to the slow signal; said processor means responsive to a continued material flow change is operative to switch the device output to be equal to the fast signal; and said processor means responsive to the continued absence of a material flow change is operative to switch the device output to be equal to the slow signal.

7. The method of measuring material flow by minimizing statistical deviation in the output signal of a radiation detector comprising the steps of:
    (a) sensing and generating a fast time constant signal from the output signal of said detector;
    (b) sensing and generating a slow time constant signal from the output signal of said detector;
    (c) determining divergence of said fast and slow time constant signals; and
    (d) responding to said divergence between the fast and slow time constant signals to produce a smooth and coherent device output for controlling material flow.

8. The method of claim 7, including: determining the threshold of statistical deviation present in said output of said detector; and comparing the said threshold and the divergence of said fast and slow time constant signals, whereby said responding is in response to a divergence and a real time threshold established from said detector output.

9. The method of claim 7, including: switching the value of the fast time constant signal to be the value of the slow time constant signal to avoid perturbations in the device output.

10. The method of claim 7, including: switching the value of the device output to be equal to the value of the slow time constant signal during periods of absence of material flow changes.

11. The method of claim 7, wherein said smooth and coherent device output is provided by:
    (a) switching the value of the fast time constant signal to be the value of the slow time constant signal following a divergence of said fast and slow time constant signals;
    (b) switching the device output to be equal to the fast time constant signal following a divergence of said fast and slow time constant signals;
    (c) switching the value of the fast time constant signal to be the value of the slow time constant signal following the end of a divergence of said fast and slow time constant signals; and
    (d) switching the device output to be equal to the slow time constant signal following the end of the divergence of said fast and slow time constant signals.

12. The method of determining the density of a material flowing past a station comprising:
   (a) emitting a nuclear radiation;
   (b) flowing a material to be measured for flow rate in the path of the radiation;
   (c) detecting said radiation as affected by said material;
   (d) filtering the radiation detected to provide a signal with a fast time constant;
   (e) filtering the radiation detected to provide a signal with a slow time constant;
   (f) deriving the expected deviation threshold from the event rate of the detected radiation;
   (g) continually determining the difference between the fast and the slow signals;
   (h) comparing said differences with said threshold to determine process changes;
   (i) switching the value of the fast signal to be equal to the slow signal in response to a process change;
   (j) switching the device output to be equal to the fast signal in response to said process change;
   (k) switching the value of the slow signal to be equal to the fast signal in response to an end of process change; and
   (l) switching the device output to be equal to the slow signal in response to said process change.

* * * * *